(12) United States Patent
Zahrte, Sr. et al.

(10) Patent No.: US 6,218,744 B1
(45) Date of Patent: Apr. 17, 2001

(54) UNINTERRUPTIBLE POWER SUPPLY AND FERRORESONANT TRANSFORMER FOR USE THEREWITH

(75) Inventors: Donald K. Zahrte, Sr., Necedah; Peter Jungwirth, Wisconsin Rapids, both of WI (US)

(73) Assignee: Powerware Corporation, Raleigh, NC (US)

( * ) Notice: Subject to any disclaimer, the term of this patent is extended or adjusted under 35 U.S.C. 154(b) by 0 days.

(21) Appl. No.: 09/532,226

(22) Filed: Mar. 22, 2000

Related U.S. Application Data
(60) Provisional application No. 60/125,461, filed on Mar. 22, 1999.

(51) Int. Cl.[7] .................................................. H02J 7/00
(52) U.S. Cl. ............................. 307/64; 307/66; 307/87
(58) Field of Search .......................... 307/64, 66, 87, 307/83; 323/248, 255

(56) References Cited

U.S. PATENT DOCUMENTS

| | | | |
|---|---|---|---|
| 4,692,854 | 9/1987 | Baxter, Jr. et al. | 363/75 |
| 4,748,341 | * 5/1988 | Gupta | 307/64 |
| 4,916,329 | * 4/1990 | Dang et al. | 307/66 |
| 5,182,518 | * 1/1993 | Stich et al. | 307/66 |
| 5,602,462 | 2/1997 | Stich et al. | 323/258 |

* cited by examiner

*Primary Examiner*—Shawn Riley
(74) *Attorney, Agent, or Firm*—Leydig, Voit & Mayer, Ltd.

(57) ABSTRACT

A line-interactive single conversion uninterruptible power supply (UPS) utilizing a multiple tapped ferroresonant transformer and a square wave PWM inverter is presented. During normal utility line operation, the line voltage is not modified in any way, except for ferroresonant filtering and regulation. Tap control circuitry insures proper tap selection based on the utility input voltage. During tap transitions in utility out of specification operation, a second power source, such as an inverter, is operated to provide output power to the connected loads. The control of the inverter switching angles may be accomplished through a look-up table. This look-up table contains the converter pulse widths for monitored battery voltage. No output voltage feedback is required. Based on the inherent regulation provided by the ferroresonant transformer, the PWM control may be accomplished in course steps.

57 Claims, 12 Drawing Sheets

UNINTERRUPTIBLE POWER SUPPLY AND FERRORESONANT TRANSFORMER FOR USE THEREWITH

RELATED APPLICATION

This application claims the benefit of U.S. Provisional Application Ser. No. 60/125,461, filed Mar. 22, 1999, the teachings and disclosure of which are hereby incorporated in their entirety by reference thereto.

FIELD OF THE INVENTION

This invention is directed to ferroresonant transformer coupled uninterruptable power supplies (UPS), and more particularly to ferroresonant transformer coupled uninterruptable power supplies utilizing pulse width modulated (PWM) inverters.

BACKGROUND OF THE INVENTION

As our society and the world continue to immerse itself in the technology and information revolution, our reliance on the electronic machines and computers that enable this technology continues to increase. From laptop PCs to complex mainframes, from fax machines to global telecommunications networks, from our personal FAX to the corner ATM, from e-mail to the Internet, from life saving and life sustaining medical equipment to computer controlled space exploration, and from personal convenience to national security, we are inextricably linked. Our lives, in many ways, exist within the critical data and processes computers and databases too numerous to count.

Along with the increasing reliance on computers and other sensitive electronic equipment comes the need to ensure that these machines remain reliably operative 24 hours a day, 365 days a year. While various methods exist to ensure data fidelity and machine operability and redundancy, it is clear that without electrical power the current revolution would quickly come to a standstill. Indeed, even the smallest disruption in electrical power can cause damage to a computer, a network, or other sensitive electronic equipment such as point-of-sale and process control equipment. At the very least, power problems can cause unexpected shutdowns and damage equipment. At the worst, bad power quality can cause data loss or corruption, or even destroy equipment. Even minor power problems can cost a company money. Any time a power interruption delays work in progress; valuable time is lost, and lost time means lost money.

While many are aware of the obvious problem of electrical power outages or blackouts that are usually caused by faults on the utility power system, there are many other power problems that can corrupt or destroy critical data, and damage equipment. Transients or power spikes, for example, caused by lightning or the switching of electrical loads can also destroy electronic circuitry and corrupt stored data. Likewise, power surges and overvoltages commonly caused by large electrical load changes and from utility power line switching can seriously damage electrical equipment. Further, power sags and brownouts that commonly occur when motors are started or as a result of a lack of capacity or faults in the power system can also cause sudden shutdowns in computer or process control equipment.

In recognition of these problems, uninterruptable power supplies (UPS) have been developed to provide, as their name implies, an uninterruptable and more robust (less prone to power problems described above) source of electrical power to sensitive electronic equipment. These UPSs are interposed between the sensitive electronic equipment and the electric utility input. They typically include a battery and power inverter that is capable of supplying AC power to the electronic equipment in the event of power loss or loss of power quality at the utility input. The power inverters may take many forms, but typically employ a sophisticated pulse-width modulated (PWM) scheme to convert the DC power from the battery to AC power for use by the electronic equipment. To avoid the requirement of large or multiple series connected batteries, linear transformers are typically used to step-up the inverter output AC voltage.

Unfortunately, the control algorithms required by these inverters to turn the power switches (typically insulated gate bipolar transistors (IGBTs)) on and off to construct a clean AC waveform are quite complex and require substantial computing power. The switching angle control is quite sensitive to variations in the attached load and requires highly accurate feedback circuitry to monitor the output voltage. Since the inverter is isolated from the output load by the linear transformer, a feedback signal transformer and other external circuitry are typically employed to provide the output voltage information to the controller for use in the control algorithms. This substantially increases the cost and complexity of the UPS system.

Depending on the sensitivity of the equipment to be powered, the UPS may allow the utility to supply power during normal operation, and may only switch to battery/inverter power during times of power outages or poor power quality. However, because utility power may experience sudden power problems as described above, most UPSs also include filtering to ensure that transients and other power glitches are not passed through to the equipment. In other words, additional circuitry is needed to provide output voltage regulation. This also increases the cost and complexity of the UPS system.

As an alternative to using a linear transformer and external regulation circuitry, the UPS described in U.S. Pat. No. 4,692,854, entitled *Method and Apparatus for Modulating Inverter Pulse Width*, issued to Baxter, Jr. et al., employs the use of a non-linear device known as a ferroresonant transformer. With its inherent regulation capability, this ferroresonant transformer is used to couple both the input AC voltage from the utility and the generated AC voltage from the inverter to the loads. While this design provides excellent performance, the control algorithms necessary for controlling the inverter to operate just outside of input saturation of the transformer are complex. These complexities are necessary in this prior design to avoid allowing the transformer to reach full core saturation. If the ferroresonant transformer were to reach full core saturation, the current would rise dramatically, would possibly cause component damage, and would certainly increase power dissipation.

As will be recognized by one skilled in the art, when a transformer saturates, the current it draws will ramp up after being stable for a period of time. Traditional saturation regulation depends on the detection of this ramp to shut off the switching devices. One of the disadvantages of this method is that any power put into the transformer after the saturation point is either dissipated as heat in any external snubbing circuitry (push-pull) or is dumped back into the battery (H-bridge). In either case, this energy is not available to the load during this time. Lastly, this method makes the power devices switch the resulting high current during saturation, resulting in higher switching losses. Both of these factors add up to less efficiency in the inverter.

As an alternative to saturation regulation that alleviates some of its drawbacks, regulation via feedback from the output voltage has also been attempted. Algorithms using output voltage feedback generally calculate an error between the present output voltage and the desired output voltage. This difference is then used to adjust the pulse width of the inverter accordingly. However, a signal transformer and other external circuitry are needed for this method because the output of the transformer is isolated from the inverter side of the system. This increases the complexity and expense of the system.

In addition to the complexities of current PWM algorithms, the physical size of the ferroresonant transformers used in these conventional systems is quite large and heavy. This size problem is driven mainly by the input voltage range from a typical utility, which can swing from 87 Vrms to nearly 148 Vrms for a standard 120 Vrms utility. To accommodate this voltage swing, the typical ferroresonant transformer requires that the input winding for the utility input use relatively large wires. This additional copper (larger wires) is necessary to handle the increased current draw through the primary that is required to supply a relatively constant output power to the load without overheating. That is to say, as the input voltage droops, the input current must increase to supply the same output power.

At the high voltage end of the spectrum, typical ferroresonant transformers require additional ferromagnetic material, typically steel, in the laminations to prevent saturation of the input core. As discussed above, saturation of the input core would result in a dramatic rise in input current and power dissipation, and could possibly damage the system. Such required robustness results in a typical ferroresonant transformer rated at approximately 3 kVA weighing approximately 75 pounds.

Therefore, there exists a need in the art for a new and improved UPS that overcomes these and other problems existing in the art. More specifically, there exists a need in the art for a new and improved UPS that does not require complex controls and sophisticated sensing circuitry for control of the PWM inverter during battery powered operation. Further, there exists a need for a UPS which includes a ferroresonant transformer that is lighter in weight, but that can still reliably operate over the utility input voltage range without overheating the input windings or saturating the input core.

SUMMARY OF THE INVENTION

It is a feature that the UPS utilizes a PWM inverter driven by a coarse switching control. It is a further feature that the coarse switching control operates without UPS output voltage sensing or other high resolution sensing circuitry, thereby simplifying the system design. Additionally, it is a feature that the coarse switching control may use a look-up table of switching control points while providing quality power output. In view of this feature, it is an additional feature that the inverter control may be accomplished in a simple programmable logic array (PLA), application specific integrated circuit (ASIC), etc. in addition to in a microprocessor. If a microprocessor is used, it is a feature that the switching control may utilize an algorithm requiring substantially less computing power than algorithms heretofore used, and may simply employ the look up table discussed above.

It is also a feature to provide a UPS utilizing a multiple-tapped ferroresonant transformer of substantially reduced size and weight compared to conventional ferroresonant transformers designed for a comparable input voltage range. It is a further feature to utilize a tap-switching controller that maintains an appropriate input-winding configuration based on the input voltage from the utility. It is a further feature to utilize an output compensation winding to aid in the production of a sine wave output to the loads. It is an additional feature that the ferroresonant transformer maintains an output waveform during break power transitions from the utility input to the inverter, and vise versa.

In one aspect, the invention provides an uninterruptable power supply (UPS) that includes a ferroresonant transformer having a first input winding adapted to be coupled to an external primary source of power, a second input winding, and an output winding. The first input winding also contains two or more winding taps. The UPS also includes an output tank capacitor coupled across the output winding and the compensation winding and a secondary power source coupled to the second input winding. Two or more tap-switching relays are interposed between the two or more winding taps and the external primary source of power. Each of the tap-switching relays selectively couples the external source of power to one of the winding taps. The UPS also includes a controller in sensory communication with a voltage of the external source of power. This controller selectively commands the tap-switching relays to open and close based on the sensed voltage.

In a further embodiment, the controller commands all of the tap-switching relays open before commanding a change in configuration of the tap-switching relays. This is accomplished in response to a change in the voltage. The controller further utilizes two or more, and preferably three predetermined threshold values to determine a proper configuration of the tap-switching relays. Preferably, the UPS also includes a static switch interposed between the input winding and the external source of power. In this embodiment, the controller commands the static switch off prior to commanding all of the tap-switching relays open, and commands the secondary power source to operate after commanding the static switch off. The controller further commands the secondary power source to stop operating prior to commanding the static switch on and after commanding one of the tap-switching relays to close.

Additionally, the ferroresonant transformer further includes a compensation winding coupled in series with the output winding. The first input winding preferably also include at least three winding taps, and at least three tap-switching relays. These relays are interposed between the three winding taps and the external primary source of power, and selectively couple the external source of power to one of the winding taps. The controller is adapted to utilize at least three predetermined threshold values to determine a proper configuration of the tap-switching relays. In a further embodiment, the tap-switching relays are solid state switching devices. Alternatively, the tap-switching relays are electromechanical devices. In such an embodiment, the UPS further includes a static switch interposed between the tap-switching relays and the external source of power.

In an alternate embodiment, each of the winding taps is positioned approximately 15% from an adjacent winding tap. In an embodiment wherein the transformer includes a first, a second, and a third winding tap, the first winding tap is positioned on the input winding to provide a first turns ratio, the second winding tap is positioned on the input winding to provide a second turns ratio, and the third winding tap is positioned on the input winding to provide a third turns ratio. Preferably, the first turns ratio is approximately 15% less than the second turns ratio and the third turns ratio is approximately 15% greater than the second turns ratio. In a further aspect the first turns ratio is approximately 88% of the second turns ratio and the third turns ratio is approximately 115% of the second turns ratio. Preferably, the controller is adapted to control the tap changing relays to maintain a maximum voltage swing across the first input winding to approximately +/−10%.

The secondary source of power preferably includes a battery and an inverter. The controller provides inverter control commands to operate the inverter in accordance with a monitored voltage of the battery. While the controller may calculate the inverter control values itself, preferably the controller contains a look-up table of inverter control values associated with the monitored voltage of the battery. The inverter control values are precalculated in accordance with $$\tau_{on} = \left( \frac{V_{RMS}}{\text{Turns ratio} \cdot (V_{battery} - V_{drop})} \right)^2 \cdot \tau_{half\ cycle},$$

and the controller operates open loop with regard to voltage at the ferroresonant transformer output, where:

$V_{RMS}$ = RMS voltage required on the input winding $= \frac{\text{Desired primary voltage}}{\text{Transformer turns ratio}}$;

$V_{peak}$=Peak voltage across winding=$V_{battery}$−$V_{drop}$;

$V_{drop}$=Voltage drop in the inverter path, which is dominated by the switching device drop;

$\tau_{half\ cycle}$=½ of the operating line frequency (e.g. 50 Hz or 60 Hz) of the ferroresonant transformer 18; and $\frac{\tau_{on}}{\tau_{half\ cycle}}$ = duty cycle.

Further, the controller operates open loop with regard to the voltage at the ferroresonant transformer output. Additionally, the controller is adapted to control the inverter to alternate between a power pulse and a freewheel mode of operation. In accordance with one aspect, the inverter includes four switches configured in an H-bridge configuration. Alternatively, the inverter includes three switches configured in a push-pull configuration.

In an alternate embodiment, a power supply includes a ferroresonant transformer having an input winding, an output winding, and a compensation winding coupled to the output winding. A tank capacitor is coupled across the output winding and the compensation winding. Further, an inverter having an input coupled to a source of dc power and an output coupled to the input winding is included. This inverter further has a plurality of controllable switches operable to construct a square wave voltage on the output of the inverter (which is input to the transformer) from the dc power on the inverter's input. A controller having stored therein a table of pre-calculated inverter switch control signals associated with voltage levels of the source of dc power is also included. This controller monitors the voltage level of the source of dc power and selects the inverter switch control signals based thereon. Further, the inverter generates a square wave on the output in response to the inverter switch control signals.

In a further embodiment of this power supply, the inverter control signals control a pulse width of the inverter switches. Preferably, the control signals in the table are limited to signals that will generate even pulse widths. In a preferred embodiment, the inverter switch control values are precalculated in accordance with $$\tau_{on} = \left( \frac{V_{RMS}}{\text{Turns ratio} \cdot (V_{battery} - V_{drop})} \right)^2 \cdot \tau_{half\ cycle}.$$

The controller also preferably operates to control the inverter in open loop with respect to the output winding. The controller is further adapted to control the inverter to alternate between a power pulse and a freewheel mode of operation. In accordance with one aspect, the controllable switches include four switches configured in an H-bridge configuration. In an alternate aspect, the controllable switches include three switches configured in a push-pull configuration.

In yet a further embodiment of this power supply, two or more, and preferably three tap changers, each having an input adapted to be coupled to a source of ac power and an output are included. The ferroresonant transformer further includes a utility input winding having two or more, and preferably three taps associated therewith, and wherein each of the outputs of the two or more, and preferably three tap changers are coupled to one of the taps. The controller may further control selection of one of the tap changers based on a monitored voltage of the source of ac power.

The ferroresonant transformer further includes a compensation winding coupled in series with the output winding. Additionally, the utility input winding further includes at least three winding taps, and at least three tap changers interposed between the three winding taps and the source of ac power. The controller is adapted to utilize at least three predetermined threshold values to determine a proper configuration of the tap changers. In one embodiment the tap changers are solid state switching devices. Alternatively, the tap changers are electromechanical devices. In this embodiment the power supply further includes a static switch interposed between the tap changers and the source of ac power.

In accordance with another aspect of the invention, each of the winding taps is positioned approximately 15% from an adjacent winding tap. Alternatively, in an embodiment wherein the transformer includes a first, a second, and a third winding tap, the first winding tap is positioned on the utility input winding to provide a first turns ratio, the second winding tap is positioned on the utility input winding to provide a second turns ratio, and the third winding tap is positioned on the utility input winding to provide a third turns ratio. In this embodiment, the first turns ratio is approximately 15% less than the second turns ratio. Further, the third turns ratio is approximately 15% greater than the second turns ratio. Preferably, the first turns ratio is approximately 88% of the second turns ratio and the third turns ratio is approximately 115% of the second turns ratio. In accordance with yet another aspect of the invention, the controller is adapted to control the tap-changers to maintain a maximum voltage swing across the first input winding to approximately +/−10%.

In another aspect, the invention provides a ferroresonant transformer for use in a power supply. The power supply supplies electric power to output connected loads from a utility ac input having a regulated voltage range bound by an upper and a lower voltage value. This transformer includes a ferromagnetic core, and a primary winding wound on the core having a first and a second tap. In an alternate embodiment, a third tap is included. For embodiments that contain greater or fewer taps, they are each positioned proportional to their number to divide the input voltage range therebetween. The transformer also includes an output winding wound on the core and separated from the primary winding by a first magnetic shunt. The ferromagnetic core contains an amount of ferromagnetic material insufficient to prevent saturation of the primary winding at the upper voltage value of the utility voltage range when the upper voltage value of the utility voltage range is coupled to one of the second and the third taps.

Preferably, the first and the third taps are positioned within approximately +/−15% of the second tap, respectively, and preferably within +12% and −9% respectively. The ferromagnetic material of the core is preferably steel, and preferably in the form of steel laminations, although other core constructions known in the art are applicable as well. The primary winding further includes a wire of a size insufficient to prevent overheating of the winding at the lower voltage value of the utility voltage range when the lower voltage value of the utility voltage range is coupled to one of the first and the second taps at rated load. The transformer preferably further includes a compensation winding wound on the steel core and separated from the output winding by a second magnetic shunt, and coupled to the output winding. An output tank capacitor is also coupled to the output winding and the compensation winding. This output tank capacitor has a VA rating that is insufficient to regulate the transformer output over the utility voltage range without selectively switching the utility ac input between the first, the second, and the third taps.

In accordance with an alternate aspect of the invention, the first tap is positioned approximately 15% from the second tap, and the second tap is positioned approximately 15% from the third tap. Preferably, the first tap is positioned on the first primary winding to provide a first turns ratio, the second tap is positioned on the first primary winding to provide a second turns ratio, and the third tap is positioned on said utility input winding to provide a third turns ratio. In this embodiment, the first turns ratio is approximately 15% less than the second turns ratio and the third turns ratio is approximately 15% greater than the second turns ratio. Preferably, the first turns ratio is approximately 88% of the second turns ratio and the third turns ratio is approximately 115% of the second turns ratio. In accordance with another aspect, the taps are positioned on the first input winding to maintain a maximum voltage swing across the first input winding to approximately +/−10% over the regulated voltage range.

The transformer of the invention preferably includes a second input winding wound on the core. Alternatively, the transformer includes a compensation winding wound on the core and separated from the output winding by a magnetic shunt. Preferably, this compensation winding is coupled in series with the output winding. In accordance with another aspect of the invention, the ferromagnetic core is constructed from a number of steel laminations. This number is substantially less than the number of steel laminations that are required to prevent saturation of the primary winding over the regulated voltage range of the utility ac input without the taps. In one embodiment, the number of steel laminations is approximately 20% less than the number of steel laminations required without the taps. In another embodiment, the number of steel laminations is approximately 30% less than the number of steel laminations required without the taps.

In view of the above it is, therefore, an advantage to provide a new and improved UPS that utilizes a simplified PWM control technique. It is an additional advantage to provide a new and improved UPS that is smaller and lighter for a given power rating. It is also an advantage to provide a new and improved UPS that provides better output voltage regulation over a larger utility input voltage variation.

Other features and advantages of the invention will become more apparent from the following detailed description when taken in conjunction with the accompanying drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1A:
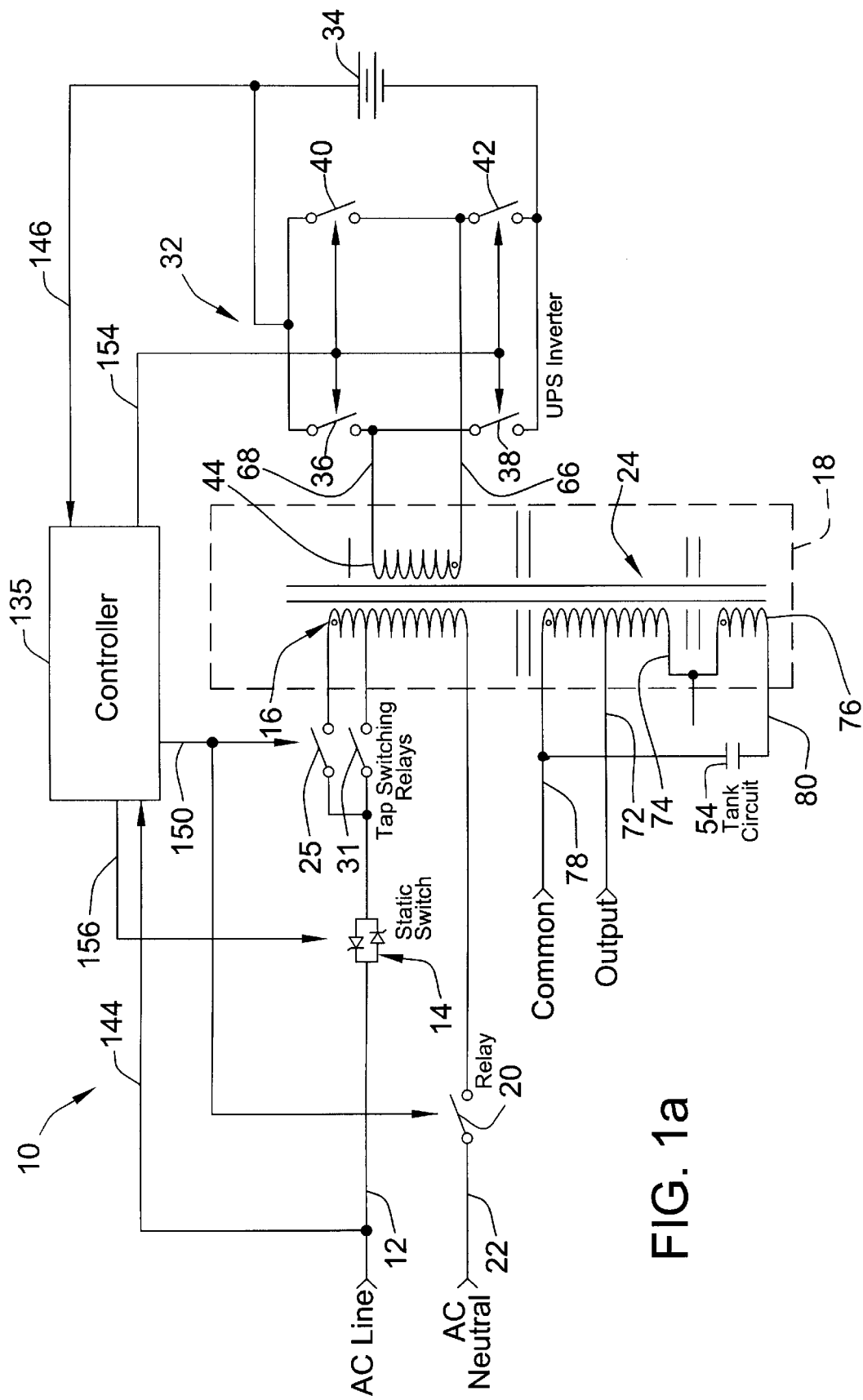
FIGS. 1a–d are schematic illustrations of alternate embodiments of a line-interactive single conversion UPS according to exemplary aspects of the invention.
Figure 7:
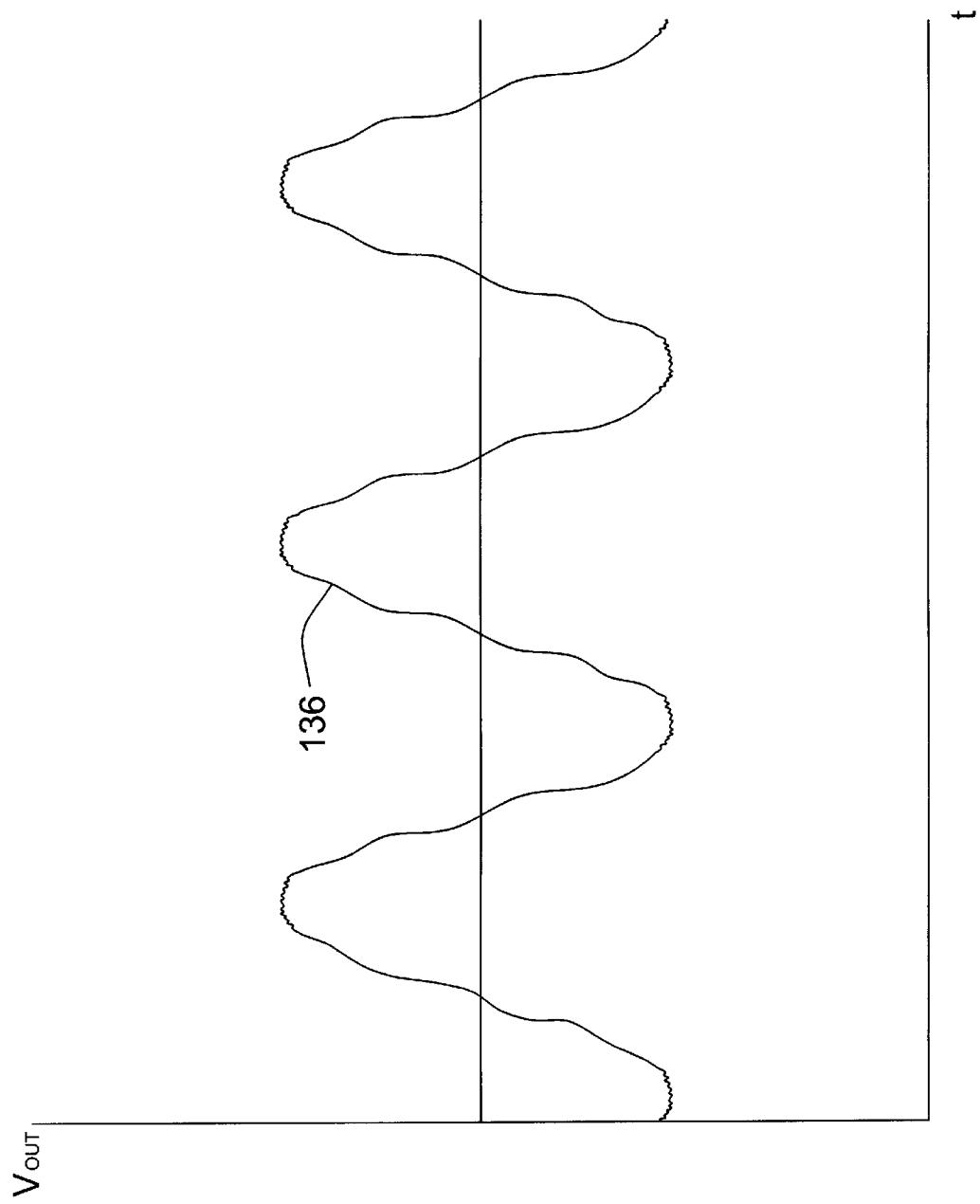
FIG. 7 is a graphical illustration of a waveform achievable through an embodiment of the invention.

An embodiment of a line-interactive single conversion UPS is illustrated in FIG. 1a to which specific reference is now made. During normal utility line operation, the line voltage is not modified in any way, except for ferroresonant filtering and regulation as illustrated by the output waveform 136 illustrated in FIG. 7. The power path during such operation is from the utility input line 12, through a static switch 14, through one of a series of tap switching relays 25 and 31 (the selection and control of which will be discussed below), through a primary winding 16 of a ferroresonant transformer 18, back through a backfeed relay 20 to the utility neutral line 22. The connected loads are powered through the secondary/tank circuit 24 of transformer 18.

One skilled in the art will recognize that the static switch 14 and the backfeed relay 20 are required in some industrial applications for safety considerations, and are not necessarily required for proper operation of the UPS 10. Therefore, their inclusion should be taken as illustrative of a preferred embodiment, and not as limitations on the inventive concepts presented herein. Additionally, the particular technology employed for the tap switching relays 25 and 31 may be varied based on system requirements, i.e. solid state tap changers such as illustrated in FIG. 1c as elements 26', 28', 30' or other electronic switching devices and configurations may be employed instead of mechanical relays. These electronic switching devices may include, in addition to the back to back SCRs 26', 28', 30' of FIG. 1c, for example, IGBTs, MOSFETs, GTOs, MCTs, etc. While this list may not be exhaustive, it does present exemplary devices having switching performance that could be utilized to accomplish the switching functions required. Therefore, as used herein the term relay should not be construed to be limited to only mechanical devices.

The UPS 10 also includes an inverter circuit 32 for supplying power from an energy storage element, such as battery 34, in the event that the utility input power exceeds its normal regulation limits. This inverter circuit may be configured in an H-bridge topology comprising switches 36, 38, 40, and 42 as illustrated, or may take on other topologies, such as a push-pull configuration (see FIG. 1d). To simplify the following discussions, only the H-bridge and push-pull inverter configurations will be discussed in detail, as implementation of other topologies will be apparent to those skilled in the art from the following discussion. In the embodiment illustrated in FIG. 1a, the inverter 32 supplies its output power through an inverter primary winding 44 of transformer 18. As with the utility operation, the connected electrical loads are supplied through the secondary/tank circuit 24.

The control of this UPS 10 is coordinated through a controller 135. This controller 135 receives as inputs the AC line voltage on line 144 and the battery output voltage on line 146. The state of the tap switching relays 25 and 31, and the backfeed relay 20 is controlled by controller 135 based on the AC line input 144. The state of the static switch 14 is also controlled by the controller 135 via line 156. During inverter 32 operation, the controller 135 senses the dc battery voltage via line 146 to control the switching of the inverter switches 36, 38, 40, and 42 via control line 154. One skilled in the art will recognize that control lines 150 and 154 are represented herein as single control lines, but may actually be implemented as multiple control lines to each controlled element.

Figure 1B:
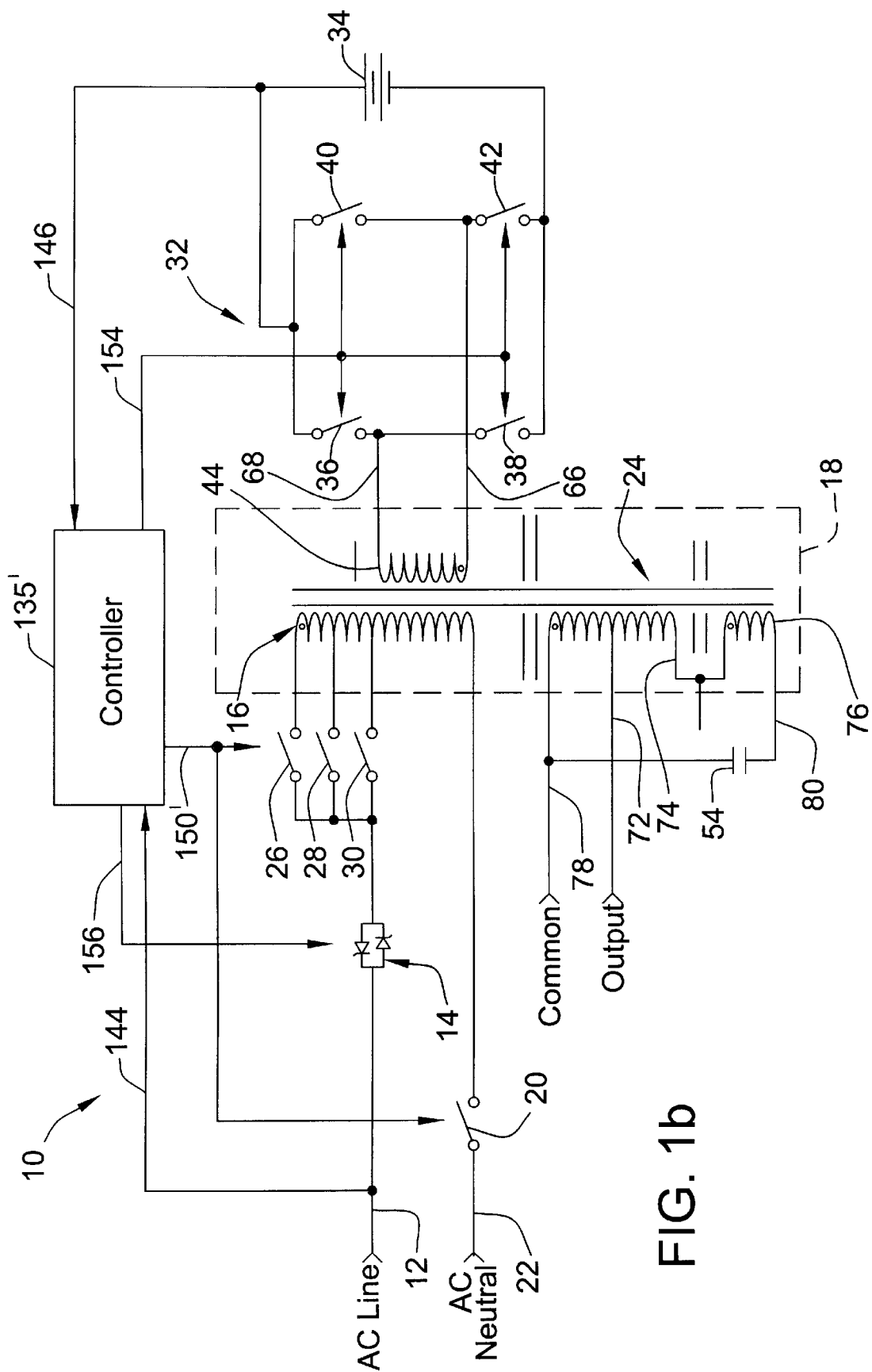
Figure 1C:
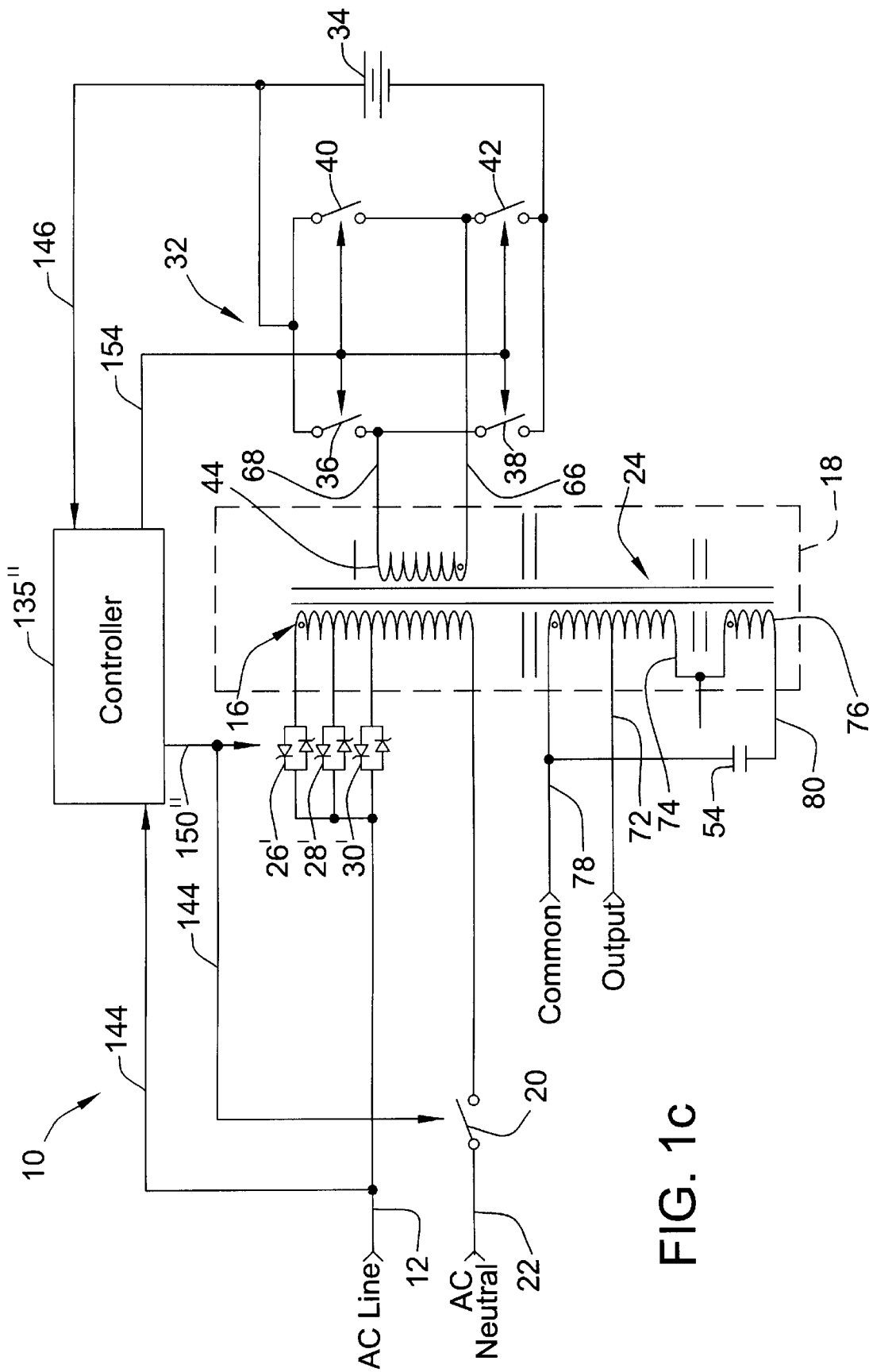

An alternate embodiment of the UPS 10 is illustrated in FIG. 1b. As may be seen from an examination of this figure, three tap changers, e.g. relays 26, 28, 30, are utilized to switch the utility AC line input 12 to the input winding 16 of the ferroresonant transformer 18. While the controller 135' for this embodiment still operates off of the same AC line input sense 144 to control the relays 26, 28, 30, the control functions vary in recognition of the different set points as reflected in control line 150'. Such control will be described more fully below with reference to FIGS. 5, 6, and 8.

As indicated above, the particular technology for the relays 26, 28, 30 is not a limiting factor in this invention. Indeed, these tap changing relays 26, 28, 30 may utilize mechanical or electromechanical technology, or solid state switching technology. One embodiment of a solid state implementation of the tap changers is illustrated in FIG. 1c. This exemplary embodiment utilizes a back-to-back SCR configuration to form AC switches 26', 28', 30'. With this embodiment, as with the other solid state embodiments, the necessity of the static switch 14 (see FIGS. 1a and 1b) is dispensed. This is because of the speed with which the solid state devices may be switched via control lines 150". Controller 135" no longer needs to be concerned with the relatively longer switching times common with mechanical type relays, and may therefore rely solely on the tap changers 26', 28', 30' themselves.

Figure 1D:
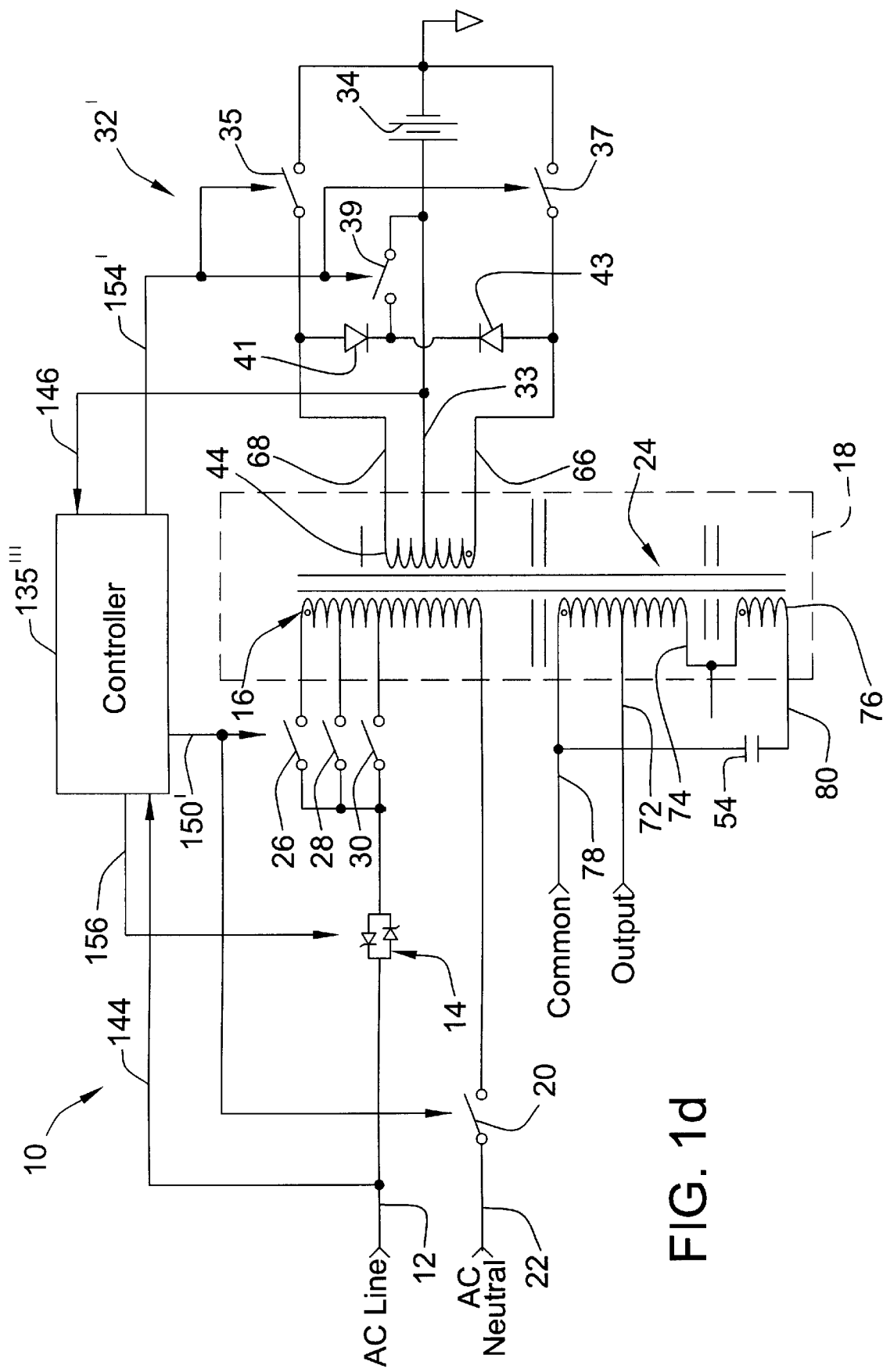

An alternate embodiment of the UPS 10 of the invention utilizing a push-pull inverter configuration 32' is illustrated in FIG. 1d. This push-pull inverter 32' couples the positive side of the battery 34 to the center of the inverter winding 44 via line 33, and couples the ends 66, 68 of the winding 44 to the negative side of the battery 34 through switches 37, 35 respectively. The inverter 32' also includes a freewheel switch 39 that shorts the inverter winding 44 through diodes 41 and 43 during the freewheel portion of the inverter cycle, described more fully below with respect to FIG. 10. The control for these inverter and freewheel switches 35, 37, 39 is provided by controller 135''' via control lines 154'. The system level operation of the inverter 32' is similar to that described above with respect to the H-bridge inverter 32 illustrated in FIG. 1a–c, in that the inverter is utilized to provide power to the system loads during periods of utility outages or transitions between input taps when mechanical or electromechanical type relays are used for tap changers 26, 28, 30.

Figure 2:
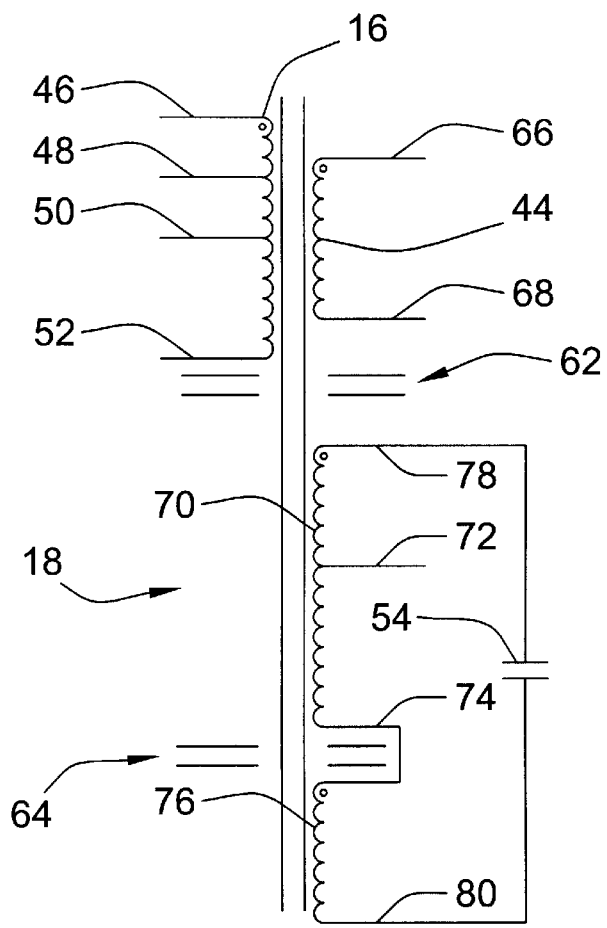
FIG. 2 is a detailed illustration of a ferroresonant transformer of the UPS of FIG. 1.

Turning now briefly to the construction of the ferroresonant transformer 18 as illustrated in FIG. 2, we note first that the utility primary input winding 16 contains, preferably, four leads 46, 48, 50, and 52. While lead 52 is the utility return lead, leads 46, 48, and 50 provide the selectable inputs to the various winding tap points on this utility primary input winding 16. Specifically, lead 48 is the nominal winding tap input, which is connected during nominal utility voltage operation. That is, lead 48 is used to provide nominal output voltage to the connected loads when the input utility voltage is between approximately 102 Vrms to approximately 125 Vrms, or a nominal voltage of 114 Vrms. The selection control of the tap switching relays 26, 28, and 30 will be described in detail below.

The positioning of the first 46 and third 50 winding taps are preferably within approximately +/−15% of the second tap 48. Lead 46 is utilized to provide a buck tap configuration having a turns ratio of approximately 88% of the nominal when the utility voltage is between approximately 120 Vrms and approximately 148 Vrms, or a nominal voltage of 132 Vrms. Finally, lead 50 is utilized to provide a boost tap configuration having a turns ratio of approximately 115% of the nominal when the utility voltage is between approximately 87 Vrms to approximately 107 Vrms, or a nominal voltage of 96 Vrms. It should be noted that while the input voltage on these taps may vary approximately +12% to −9%, the ferroresonant transformer 18 holds the output regulation to approximately +5% to −8.3%.

While the use of transformer taps is known to allow a transformer to operate over an extended input voltage range, the utilization of the tap leads in transformer 18 is unique. Specifically, the input voltage range to transformer 18 is fixed by the utility. Therefore, there would have been no conventional reason or suggestion to add such multiple input taps to a transformer whose input voltage range is fixed. Indeed, conventional wisdom in the UPS art teaches against trying to extend the input voltage range beyond that specified for the utility, because operation outside that specified range is typically indicative of a severe problem with the utility. Instead, a typical UPS switches to inverter operation under such circumstances.

However, the addition of such multiple taps, even in a system with a fixed input voltage range, allows better regulation even within this range. Surprisingly, the addition of these taps provides other substantial benefits that were unforeseen. Specifically, the addition of these taps allows for a significant reduction in the weight, and therefore the cost, of this transformer in both the input and the output circuits. As discussed above, the weight of a typical UPS ferroresonant transformer is driven by the amount of conductive material in the windings, typically copper, required to handle the low voltage, high current conditions, and is driven by the amount of ferromagnetic material required in the core to prevent saturation during the high input voltage condition.

By adding multiple taps, the maximum voltage swing seen by the transformer is significantly reduced (to a maximum of approximately 28 volts in the preferred embodiment) compared with a non-tapped transformer. In this way, the amount of ferromagnetic material required to construct the core could be reduced by as much as 20% to 30% from that required for a non-tapped transformer operating under the same utility input range. For ferroresonant transformers constructed of steel laminations, this reduction translates into fewer steel laminations required, which also reduces the physical size of the ferroresonant transformer 18. Further, the taps also allow for a reduction in the wire size, and therefore the amount of copper, for the primary winding. Additionally, the fact that these taps change the voltage swing on the primary from approximately +15%, −20% to +/−10% resulted in a 20% to 25% reduction in the AC tank capacitor 54 VA value required to regulate the transformer output. As a result, the capacitor tank winding may be reduced by an entire wire size, thus further increasing the already significant weight savings realized by this design. While actual design implementations may vary, a weight reduction from approximately 76 pounds to approximately 54 pounds for a transformer capable of supplying rated power of 3.1 kVA has been realized. This is nearly a 30% reduction in weight.

The transformer 18 also includes the inverter primary winding 44, which is coupled to the inverter 32 via leads 66 and 68. A magnetic shunt 62 separates the main secondary winding 70 from the two primary windings 16 and 44. The main line output tap lead 72 is coupled to the load, while lead 74 is coupled across magnetic shunt 64 to the compensation winding 76. The compensation winding 76 aids in the production of an output sine wave. The inductance of compensation winding 76 may be tuned with the tank capacitor 54 to help eliminate the $3^{rd}$ and the $5^{th}$ harmonic from the output waveform. Lead 78 from the main secondary winding 70 and lead 80 from the compensation winding 76 feed the tank capacitor 54 of the output circuit.

Figure 3:
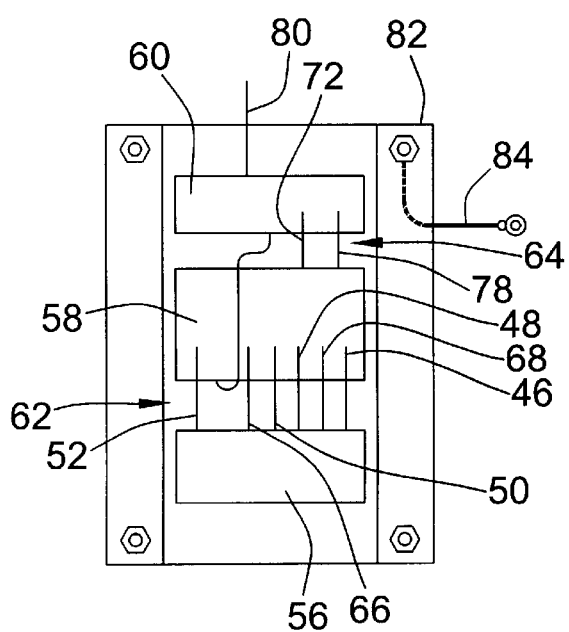
FIG. 3 is a simplified top view illustration of a ferroresonant transformer.
Figure 4:
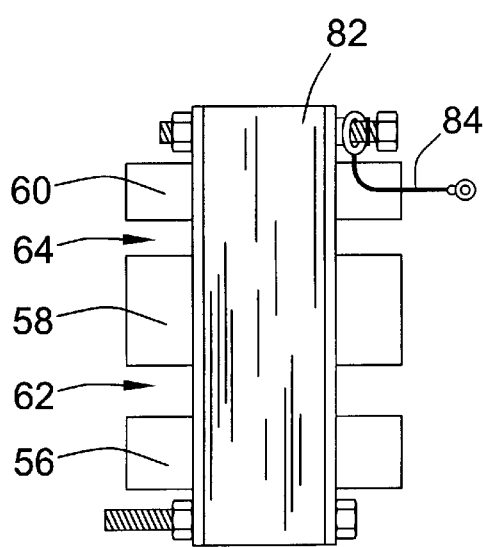
FIG. 4 is a simplified side view illustration of the ferroresonant transformer illustrated in FIG. 3.

Referring to FIG. 3, the ferroresonant transformer 18 is wound in three sections 56, 58, and 60, separated by magnetic shunts 62, 64. The transformer housing 82 is grounded in a preferred embodiment via ground lead 84. These features may be more easily appreciated from an inspection of the side view of FIG. 4.

Figure 5:
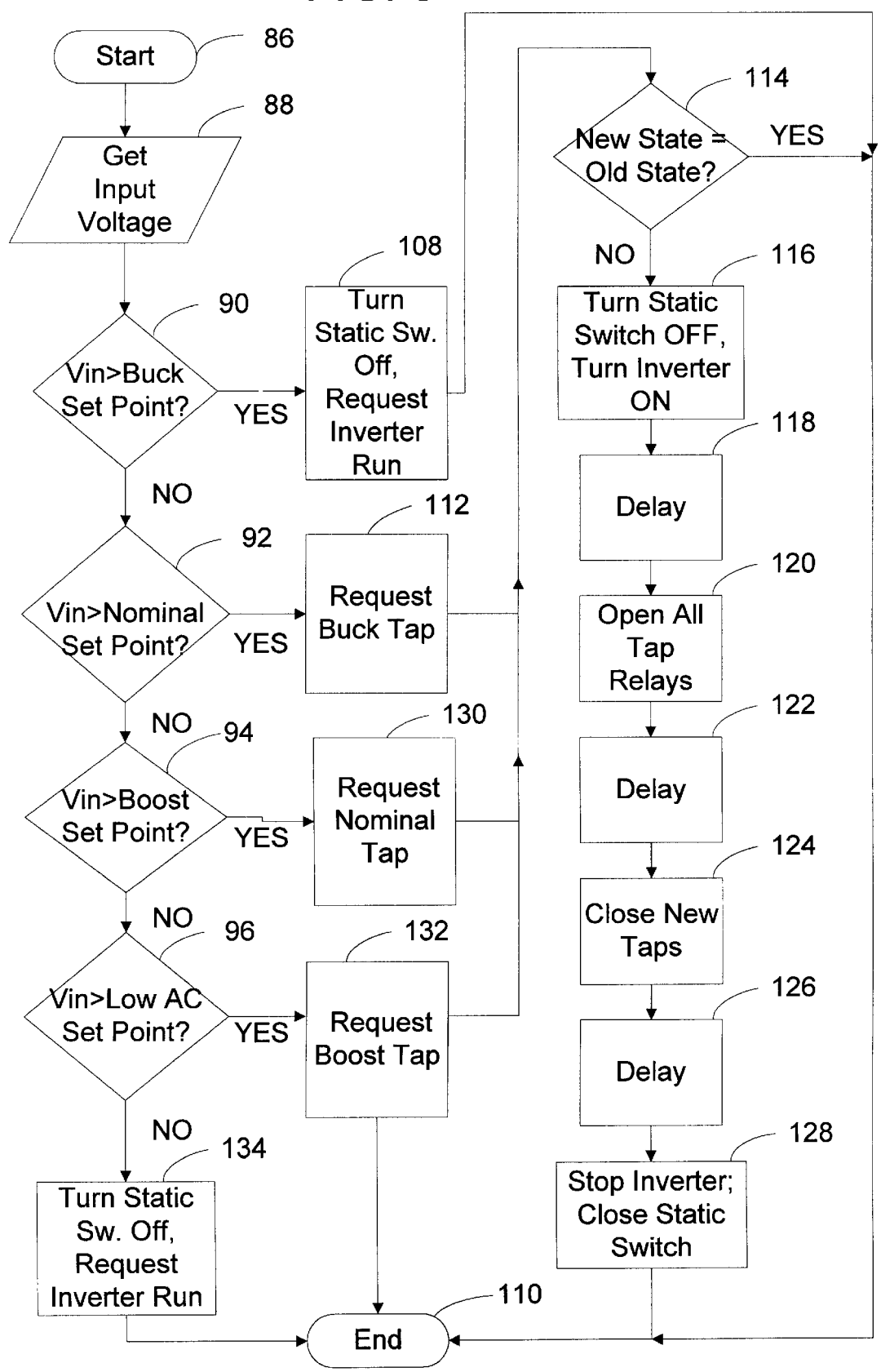
FIG. 5 is a simplified functional control flow diagram of the tap switching control according to one aspect of the invention.

Turning now away from the physical construction of an embodiment of the transformer, attention is directed to the operational flow diagram of FIG. 5 for a discussion of the operational control governing the selection of the proper input tap during utility operation. This FIG. 5 illustrates the control desired for a mechanical or electromechanical embodiment of the UPS 10, such as that illustrated in FIG. 1b. Where the control flow differs for a solid state implementation, it will be so noted in the discussion that follows. Once the process has begun at step 86, the utility input voltage is measured or its value is otherwise obtained at step 88. Once this value has been obtained, it is checked against a series of voltage threshold values at blocks 90, 92, 94, and 96. While FIG. 5 illustrates this process in a sequential flow, one skilled in the art will recognize that the system is not so limited to only this particular implementation of multiple level comparison.

Figure 6:
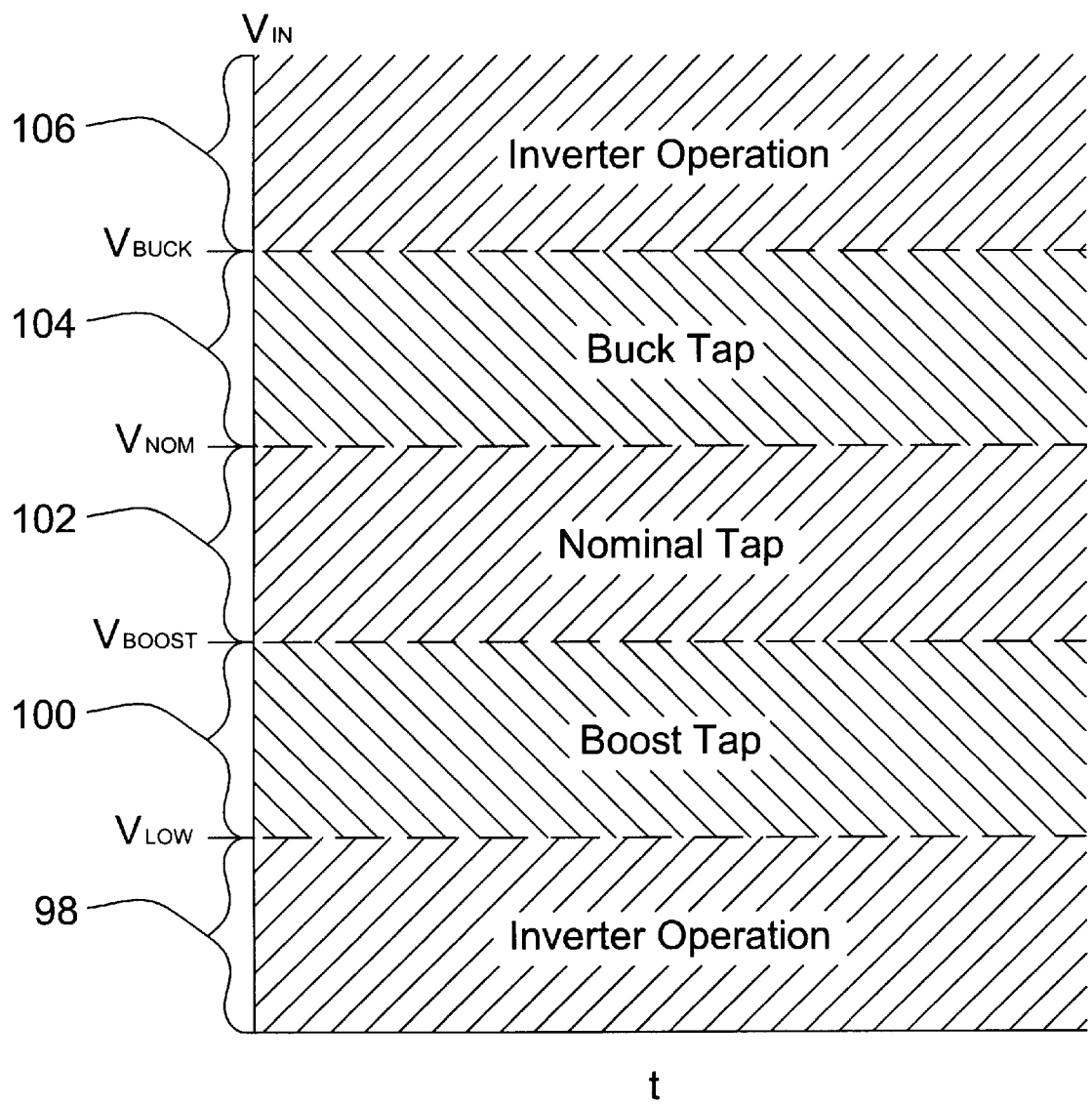
FIG. 6 is a graphical illustration of a control and operational aspect of the invention.

Indeed, it may be more instructive at this point to refer to FIG. 6, which illustrates in graphical form the various regions of exemplary operation. As illustrated, a first region of operation 98 exists between no utility voltage and its lower specified threshold $V_{low}$. As illustrated, if the utility voltage lies within this region 98, the inverter 32 is activated to power the loads. A second region 100 exists between the lower specified threshold $V_{low}$ of the utility and a boost threshold value $V_{boost}$. If the utility voltage exists between these limits, the boost tap 50 is selected and the inverter 32 is turned off or otherwise disconnected from the ferroresonant transformer 18. A third region 102 exists between the boost threshold value $V_{boost}$ and the nominal threshold value $V_{nom}$. If the utility voltage exists between these limits, the nominal tap 48 is selected. A fourth region 104 exists between the nominal threshold value $V_{nom}$ and the buck threshold value $V_{buck}$. If the utility voltage exists between these limits, the buck tap 46 is selected. A final region 106 exists above the buck threshold value $V_{buck}$. If the utility voltage exists in this region, the inverter 32 is again activated to power the loads. Of course, the utility input is disconnected by switch 14 for operation within this region 106 and that of region 98. While not illustrated in this graphical illustration, the actual implementation may include hysteresis at these switching points to prevent doorbelling operation when the utility voltage exists at approximately the threshold value.

Returning now to the illustration of FIG. 5, step 90 checks to determine if the utility input 12 voltage $V_{in}$ is greater than the buck set point $V_{buck}$. If it is, the static switch 14 is turned off and the inverter 32 is requested to run 108 to supply the connected electrical load 72, after which this cycle ends 110. If solid state devices 26', 28', 30', such as those illustrated in FIG. 1c, are utilized, step 108 would simply turn off all of the solid state tap changers 26', 28', 30' and request the inverter 32 to run since there is no static switch in that embodiment. If, however, this first condition 90 is not met, the utility input 12 voltage $V_{in}$ is checked to see if it is greater than the nominal voltage threshold $V_{nom}$ 92. If it is, the buck tap setting is requested 112. When this occurs, the system checks to determine if this state is different from the current state of the system 114. If the new state is the same as the old or current state, this cycle ends 110 without changing anything.

If, however, the two states are different, the utility input 12 is disconnected from the ferroresonant transformer 18 and the inverter 32 is commanded on while the proper tap configuration is accomplished 116. One way to accomplish this is to turn off the static switch 14 illustrated in FIG. 1. Once this has been accomplished, or after a delay sufficient for this to have been accomplished 118, the tap relays 26, 28, 30 are opened or are verified to be open 120. Once this has been accomplished, or after a delay sufficient for this to have been accomplished 122, the new tap (in this case the buck tap 46) is closed 124. Once this has been accomplished, or after a delay sufficient for this to have been accomplished 126, the inverter 32 is stopped and the static switch 14 is closed 128. This completes this cycle 110.

The transition between the utility voltage 12 and the inverter 32 results in a break power transfer at the transformer inputs, i.e. the utility input 12 is disconnected before the inverter 32 is started. While paralleling circuitry could be incorporated into the inverter control to allow a no-break power transfer between sources, this is not required in view of the operational characteristics of the ferroresonant transformer 18 and its output circuitry (tank capacitor 54). So long as the transition between sources is accomplished in a timely manner, the connected loads will not experience a break in power. This may be aided by using short processing delays between commanded actions to allow the physical devices to actuate, instead of waiting on feedback confirmation that the commanded action has been accomplished. This also reduces the requirement for this feedback thereby reducing the cost and complexity and increasing the reliability of the overall design.

Further, if electronic switching devices, e.g. tap changers 26', 28', 30' as illustrated in FIG. 1c are utilized, the system need not switch to the inverter operation during tap transitions at all. This is because the switching speed provided by the solid state devices enables a transition, preferably at a zero cross, from one tap to another, without any substantial delay whatsoever. As indicated above, in this configuration the static switch 14 and its associated control are no longer needed.

If the input voltage $V_{in}$ is not above the nominal set point $V_{nom}$, but is above the boost set point $V_{boost}$ 94, the nominal tap setting is requested 130. At this point the steps 114 through 128 are accomplished as described above. If, however this condition 94 is not satisfied, but the input voltage $V_{in}$ is greater than the low AC set point $V_{low}$ 96, then the boost tap setting is requested 132. The steps 114 through 128 are accomplished as described above. If this condition 96 is not met, then the static switch 14 is turned off and the inverter 32 is requested to run 134 to supply the connected load.

Figure 8:
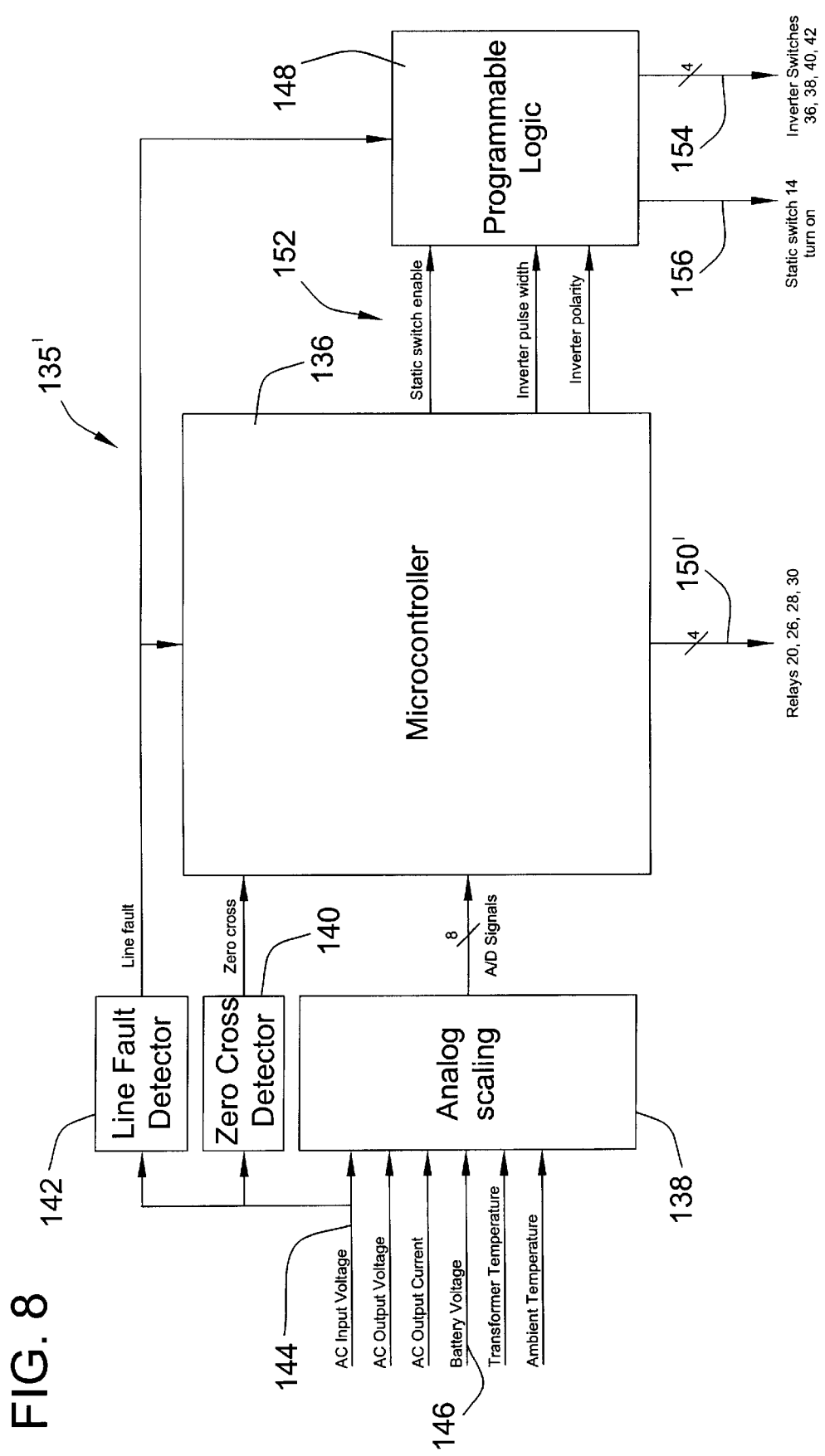
FIG. 8 is a simplified block diagrammatic illustration of a control structure of an embodiment of the invention.

Turning now to FIG. 8, a control structure 135' of a preferred embodiment is illustrated in block diagrammatic form. In its preferred form, the control structure 135' includes a microcontroller 136, which receives various control and status inputs from external circuitry, and programmable logic circuitry 148 for driving the inverter gates 36, 38, 40, 42. The external input circuitry typically includes analog scaling circuitry 138, zero cross detection circuitry 140, line fault detection circuitry 142, and other common control input circuitry. While the number and types of signals input to the microcontroller 136 may vary based on system requirements, at least the utility AC input voltage 144 and the battery voltage 146, or signals from which these parameters may be calculated, are needed for proper operation. Based on the sensed AC input voltage 144 from the utility, the microcontroller 136 determines and configures the proper input source to drive the loads as discussed in detail above. Once the proper tap configuration is determined, the microcontroller 136 commands the tap changing switches or relays 26,28,30 into their proper state via control lines 150. Coordinated operation with the inverter 32 is also accomplished by the microcontroller 136 via command signals 152 sent to the programmable logic circuitry 148. The microcontroller 136 calculates or looks up the proper pulse width for the inverter 32 based on the sensed input battery voltage 146 (this operation to be discussed more fully below). Advantageously, this requires no sensing of the output voltage from the secondary winding, and allows the controller 136 to operate in open loop with respect to the output voltage. The programmable logic circuitry 148 then actually generates the command signals to the inverter gates 36, 38, 40, 42 via control lines 154, and controls the static switch 14 via control line 156.

The basic operation of the modulation scheme drives the inverter input winding 44 of the ferroresonant transformer 18 with a square wave at the fundamental frequency desired on the output. The derivation of the duty cycle required begins with the equation:

$$V_{RMS} = V_{peak} \sqrt{\frac{\tau_{on}}{\tau_{half\ cycle}}}$$

Where:

$V_{RMS}$ = RMS voltage required on the input winding $$= \frac{\text{Desired primary voltage}}{\text{Transformer turns ratio}};$$

$V_{peak}$=Peak voltage across winding=$V_{battery}-V_{drop}$;
$V_{drop}$=Voltage drop in the inverter path, which is dominated by the switching device drop;
$\tau_{half\ cycle}$=½ of the operating line frequency (e.g. typically 50 Hz or 60 Hz) of the ferroresonant transformer 18; and $$\frac{\tau_{on}}{\tau_{half\ cycle}} = \text{duty cycle}.$$

Rearranging the terms and substituting into the equation above results in the following equation:

$$\tau_{on} = \left(\frac{V_{RMS}}{\text{Turns ratio} \cdot (V_{battery} - V_{drop})}\right)^2 \cdot \tau_{half\ cycle}$$

This equation is used to precalculate the necessary pulse width for a given battery voltage and turns ratio of the transformer. This table of pulse widths is stored, preferably, in the read only memory (ROM) of a microprocessor or microcontroller (or a PLA or other logic device) such as controller 136. At the beginning of a cycle, the control logic takes the battery voltage 146 and uses it as an offset into the ROM table containing the desired pulse width. This value is used to set the phase at which the inverter switches 36, 38, 40, 42 are turned on and a phase at which the inverter switches 36, 38, 40, 42 are turned off. The control logic 148 checks for these phase angles 32 times a half cycle in the described embodiment. As such, the resolution of the pulse width is approximately 5.6°. One skilled in the art will recognize that this equation, or variants thereof, are commonly used in conjunction with a linear transformer, which has no inherent regulation properties. However, when used with such a linear transformer, the output voltage follows the inverter voltage ($V_{battery}-V_{drop}$) by a factor of its turns ratio. As a result, any errors arising from the control circuitry resolution or device drops will be amplified by the turns ratio at the output. Because of this, when used with a linear transformer this regulation scheme requires high-resolution circuitry and an adjustment term for $V_{drop}$ based on the amount of load on the inverter.

However, because of the inherent regulation characteristics of the ferroresonant transformer 18, such high-resolution circuitry and compensation factors are not needed for the described UPS 10. In the past, traditional implementations of ferroresonant transformer based regulation schemes were dependent on feedback based either on the saturation point of the transformer or on the value of the output voltage. Each of these traditional approaches required significant and complex external feedback circuitry, and the processing of equally complex algorithms to control the inverter operation.

By using the above algorithm in conjunction with the ferroresonant transformer 18, the output voltage to the loads will be regulated so long as the inverter voltage stays within the input regulation tolerance of the transformer. This allows an implementation based on a low cost microcontroller 136, ASIC, or PLA, etc. by precalculating the pulse width for any given battery voltage, and putting these values in a look up table. Alternatively, the full implementation of this algorithm (for example, by using a higher resolution A/D converter for battery voltage and more terms for $V_{drop}$) may allow the regulation tolerance of the transformer to widen, thus reducing its cost even more.

Figure 9:
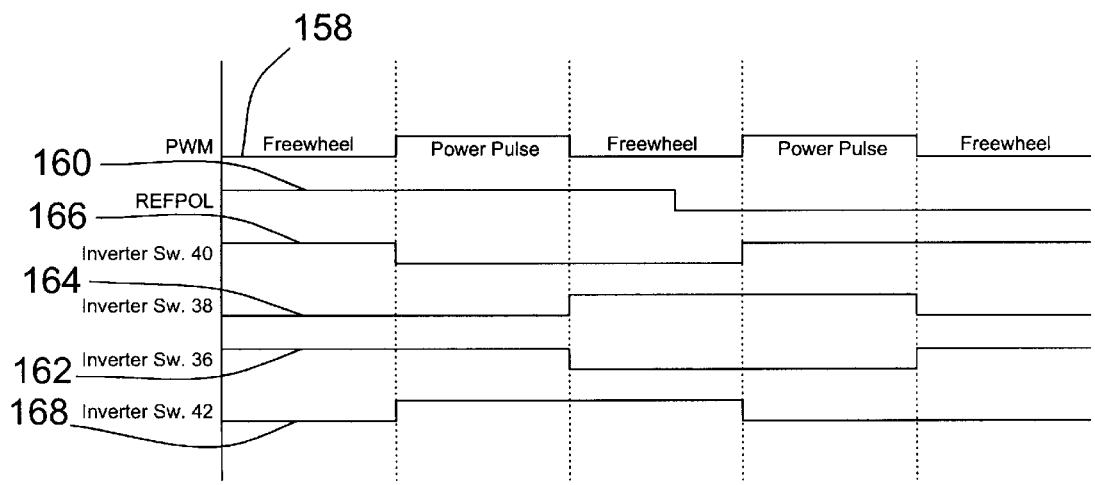
FIG. 9 is a simplified timing diagram illustrating additional control and operational aspects of the invention.

The gate drive signals 154 to each of the inverter switches 36, 38, 40, and 42 (see FIG. 1) are illustrated in the control waveform view of FIG. 9. The top trace 158 illustrates the PWM state, i.e. whether the inverter 32 is in a power pulse state or a freewheel state. In a preferred embodiment, the inverter controller freewheels (shorts the legs 66, 68 of the inverter input winding 44 of the transformer 18 together) between power pulses. This stores reactive energy in the transformer 18 that then may be used by the load. The result of this operation is that most of the energy built up during the power pulse is transferred to the load. Without this freewheel state the algorithm would have to account for the stored energy at the end of each power pulse that does not get passed to the load. This would result in a wider pulse for a given battery voltage, and would result in increased conduction losses in the switching devices 36, 38, 40, 42. Trace 160 indicates the reference polarity of the output waveform constructed by the inverter 32. Exemplary drive signals to the inverter switches 36, 38, 40, and 42 are illustrated by traces 162, 164, 166, and 168, respectively.

Figure 10:
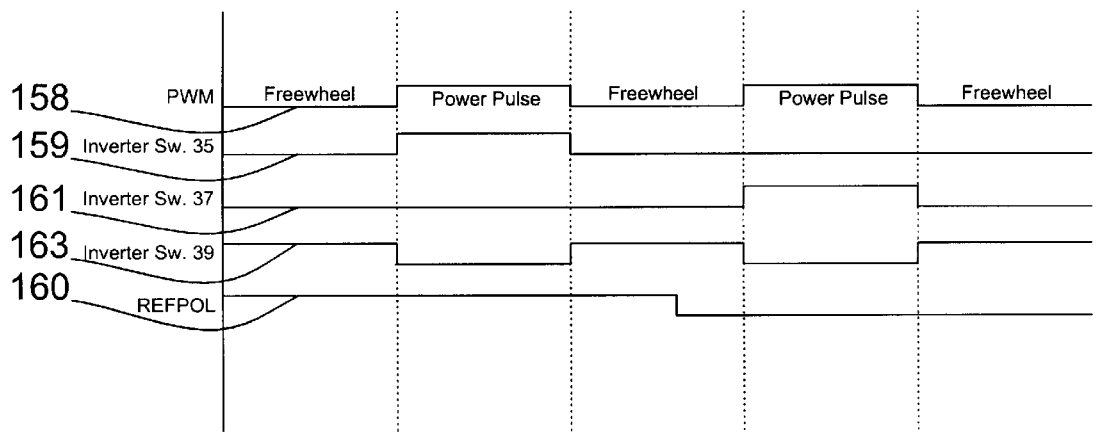
FIG. 10 is a simplified timing diagram illustrating control and operational aspects of an alternate embodiment of an aspect of the invention.

Referring to FIG. 10, the timing diagram for a push pull implementation of the power inverter (see FIG. 1*d*) is illustrated. As with the H-bridge configuration discussed above, the top trace 158 illustrates the PWM state, i.e. whether the inverter 32' is in a power pulse state or a freewheel state. In a preferred embodiment, the inverter controller 135''' freewheels (shorts the legs 66, 68 of the inverter input winding 44 of the transformer 18 together through diodes 41, 43) between power pulses. As with the above, the result of this operation is that most of the energy built up during the power pulse is transferred to the load. Without this freewheel state the inverter control algorithm would have to account for the stored energy at the end of each power pulse that does not get passed to the load. This would result in a wider pulse for a given battery voltage, and would result in increased conduction losses in the switching devices 35, 37. Trace 160 indicates the reference polarity of the output waveform constructed by the inverter 32'. Exemplary drive signals to the inverter switches 35, 37, and freewheel switch 39 are illustrated by traces 159, 161, and 163 respectively.

Figure 11:
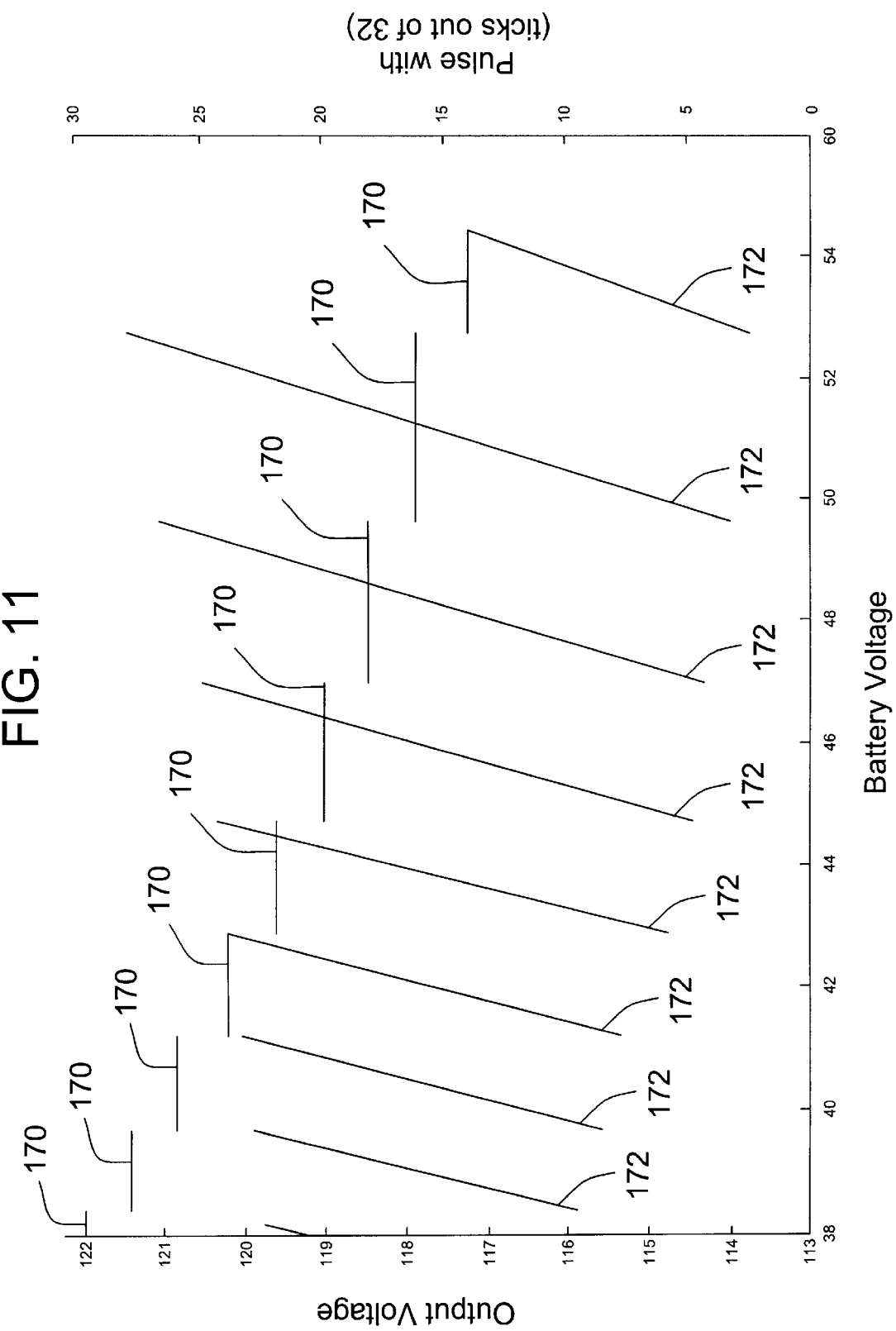
FIG. 11 is a graphical illustration of control and regulation aspects of the invention.

FIG. 11 illustrates in graphical form a table implementation of the above-described algorithm for inverter operation, and more particularly the performance of the algorithm when implemented with a microcontroller that has a pulse width resolution of 32 per half cycle, and that allows only even pulse widths. This graph is constructed for a particular embodiment of the invention with a target output voltage of 118 Vrms reflected on the AC input winding 16 and utilizing a turns ratio of 53:16. Of course, these values are presented by way of illustration only, and not by way of limitation. In this graph, the pulse width is plotted as the number of ticks out of 32 by the discontinuous steps (stored in a look-up table) identified by reference numeral 170. The resulting output voltage is plotted by trace 172. As will be recognized by one skilled in the art, the discontinuities of the PWM control 170 are reflected in discontinuities in trace 172.

During each PWM step, the reflected input voltage varies as a direct function of the variance in battery voltage 146, hence the shape of the output voltage trace 172. The width of the PWM steps, or the range of battery voltage change before a new pulse width is selected, is determined to ensure that the output voltage 172 is maintained within the regulation limits of the power requirements of the connected loads. For this particular exemplary embodiment, the steps are set in the look-up table (stored in the microcontroller 136 in this example) with the following values:

| Battery Voltage $V_{batt}$ | Pulse Width (ticks out of 32) | Inverter Duty Cycle |
|---|---|---|
| 54.4–52.9 | 14 | 43.75% |
| 52.8–49.8 | 16 | 50.00% |
| 49.7–47.1 | 18 | 56.25% |
| 47.0–44.9 | 20 | 62.50% |
| 44.8–43.0 | 22 | 68.75% |
| 42.9–41.3 | 24 | 75.00% |
| 41.2–39.8 | 26 | 81.25% |
| 39.7–38.4 | 28 | 87.50% |
| 38.3–38.0 | 30 | 93.75% |

Figure 12:
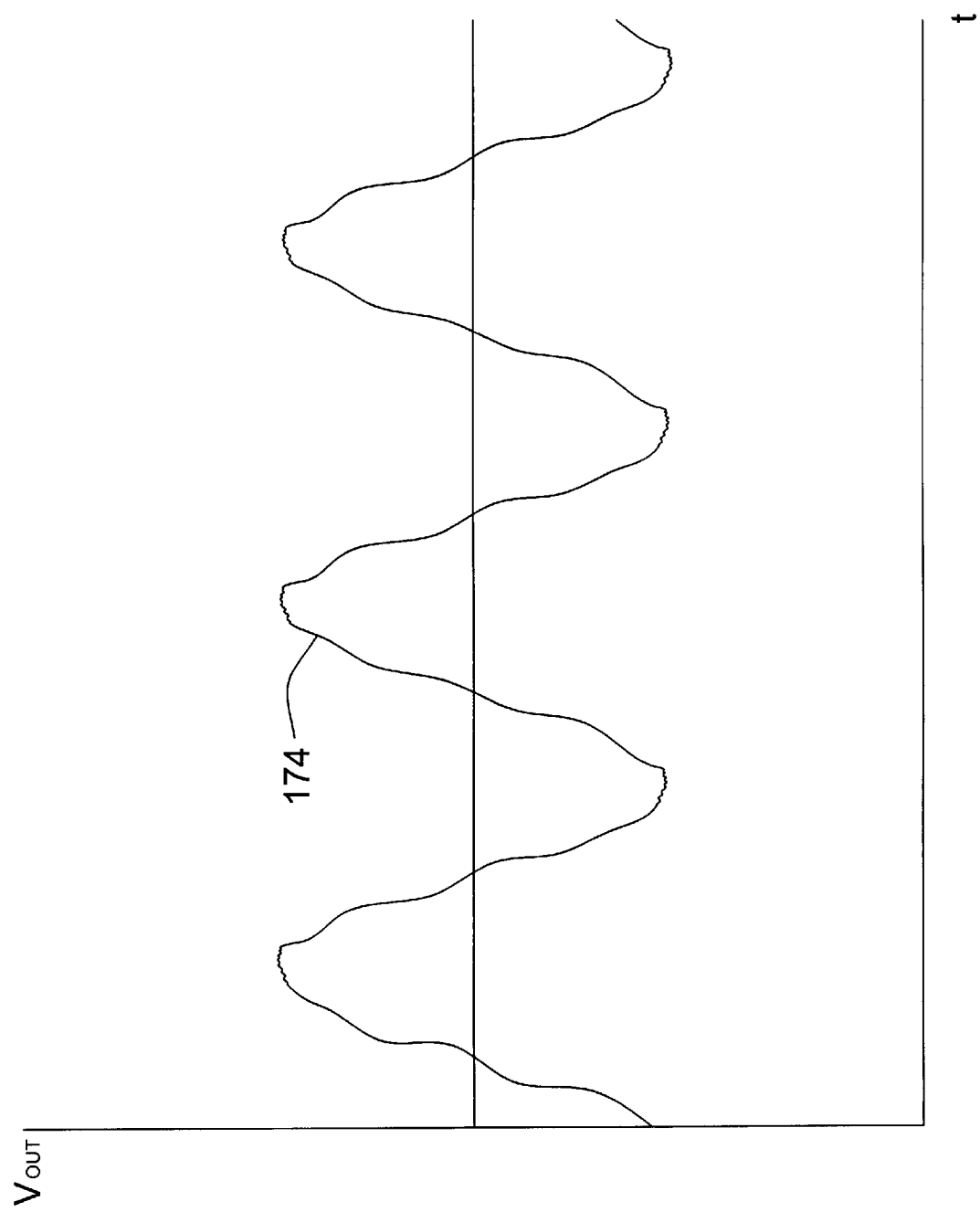
FIG. 12 is a graphical illustration of a waveform achievable through alternative operation from that illustrated in FIG. 7 of an embodiment of the invention.

The pulse width of the square wave generated during inverter operation produces a nominal RMS voltage on the inverter input winding 44, selected in this exemplary embodiment to be 34 Vrms. This voltage can vary about +12% to −9%, similar to variations as discussed above for the utility input 144 variation, and maintain proper output voltage 172 variation of approximately +5% to −8.3%. As such, the modulation can be coarse steps because the ferroresonant transformer 18 will regulate the same percentage of the nominal pulse width needed during inverter operation to drive the ferroresonant transformer 18. This allows the modulation to be set up in table form and allows simple pulse width modulation control. As a result of this modulation control and of the regulation provided by the ferroresonant transformer 18, the output voltage 172 appearing at the load 72 is as illustrated by trace 174 of FIG. 12.

Numerous modifications and alternative embodiments of the invention will be apparent to those skilled in the art in view of the foregoing description. Accordingly, this description is to be construed as illustrative only. The details of the structure may be varied substantially without departing from the spirit of the invention, and exclusive use of all modifications that come within the scope of the appended claims is reserved.

What is claimed is:

1. An uninterruptable power supply (UPS), comprising:
   a ferroresonant transformer having a first input winding adapted to be coupled to an external primary source of power, a second input winding, and an output winding, said first input winding containing at least two winding taps;
   an output tank capacitor coupled across said output winding;
   a secondary power source coupled to said second input winding;
   at least two tap-switching relays interposed between said at least two winding taps and the external primary source of power, each of said tap-switching relays selectively coupling the external source of power to one of said winding taps; and
   a controller in sensory communication with a voltage of the external source of power, said controller selectively commanding said tap-switching relays to open and close based on said sensed voltage.

2. The UPS of claim 1, wherein said controller is adapted to command all of said tap-switching relays open before commanding a change in configuration of said tap-switching relays in response to a change in said voltage.

3. The UPS of claim 2, further comprising a static switch interposed between said input winding and the external source of power, and wherein said controller is adapted to command said static switch off prior to commanding all of said tap-switching relays open.

4. The UPS of claim 3, wherein said controller is adapted to command said secondary power source to operate after commanding said static switch off.

5. The UPS of claim 4, wherein said controller is adapted to command said secondary power source to stop operating prior to commanding said static switch on and after commanding one of said tap-switching relays to close.

6. The UPS of claim 1, wherein said controller is adapted to utilize at least two predetermined threshold values to determine a proper configuration of said tap-switching relays.

7. The UPS of claim 1, wherein said ferroresonant transformer further comprises a compensation winding coupled in series with said output winding.

8. The UPS of claim 1, wherein said first input winding further comprises at least three winding taps, and further comprising at least three tap-switching relays interposed between said at least three winding taps and the external primary source of power, each of said tap-switching relays selectively coupling the external source of power to one of said winding taps.

9. The UPS of claim 8, wherein said controller is adapted to utilize at least three predetermined threshold values to determine a proper configuration of said tap-switching relays.

10. The UPS of claim 8, wherein said tap-switching relays are solid state switching devices.

11. The UPS of claim 8, wherein said tap-switching relays are electromechanical devices, the UPS further comprising a static switch interposed between said tap-switching relays and the external source of power.

12. The UPS of claim 8, wherein each of said winding taps is positioned approximately 15% from an adjacent winding tap.

13. The UPS of claim 8, wherein said transformer comprises a first, a second, and a third winding tap, and wherein said first winding tap is positioned on said input winding to provide a first turns ratio, wherein said second winding tap is positioned on said input winding to provide a second turns ratio, and wherein said third winding tap is positioned on said input winding to provide a third turns ratio, said first turns ratio being approximately 15% less than said second turns ratio and said third turns ratio being approximately 15% greater than said second turns ratio.

14. The UPS of claim 13, wherein said first turns ratio is approximately 88% of said second turns ratio and said third turns ratio is approximately 115% of said second turns ratio.

15. The UPS of claim 1, wherein said controller is adapted to control said tap changing relays to maintain a maximum voltage swing across said first input winding to approximately +/−10%.

16. The UPS of claim 1, wherein said secondary source of power comprises a battery and an inverter, and wherein said controller provides inverter control commands to operate said inverter in accordance with a monitored voltage of said battery.

17. The UPS of claim 16, wherein the controller contains a look-up table of inverter control values associated with said monitored voltage of said battery.

18. The UPS of claim 17, wherein said inverter control values are precalculated in accordance with $$\tau_{on} = \left(\frac{V_{RMS}}{\text{Turns ratio} \cdot (V_{battery} - V_{drop})}\right)^2 \cdot \tau_{half\ cycle},$$

where:

$V_{RMS}$ = RMS voltage required on the input winding $$= \frac{\text{Desired primary voltage}}{\text{Transformer turns ratio}};$$

$V_{peak}$=Peak voltage across winding=$V_{battery}-V_{drop}$;

$V_{drop}$=Voltage drop in the inverter path;

$\tau_{half\ cycle}$=½ of an operating line frequency of said ferroresonant transformer; and $$\frac{\tau_{on}}{\tau_{half\ cycle}} = \text{duty cycle}.$$

19. The UPS of claim 16, wherein said controller operates open loop with regard to voltage at said ferroresonant transformer output.

20. The UPS of claim 16, wherein said controller is adapted to control said inverter to alternate between a power pulse and a freewheel mode of operation.

21. The UPS of claim 16, wherein said inverter comprises four switches configured in an H-bridge configuration.

22. The UPS of claim 16, wherein said inverter comprises three switches configured in a push-pull configuration.

23. A power supply, comprising:
a ferroresonant transformer having an input winding, and an output winding;
a tank capacitor coupled across said output winding;
an inverter having an input coupled to a source of dc power and an output coupled to said input winding, the inverter further having a plurality of controllable switches operable to construct a square wave voltage on said output from said dc power on said input; and
a controller having stored therein a table of pre-calculated inverter switch control signals associated with voltage levels of the source of dc power, said controller monitoring the voltage level of the source of dc power and selecting said inverter switch control signals based thereon.

24. The power supply of claim 23, wherein said inverter control signals control a pulse width of said inverter switches.

25. The power supply of claim 24, wherein said control signals in said table are limited to signals that will generate even pulse widths.

26. The power supply of claim 23, wherein the inverter switch control signals are pre-calculated by $$\tau_{on} = \left(\frac{V_{RMS}}{\text{Turns ratio} \cdot (V_{battery} - V_{drop})}\right)^2 \cdot \tau_{half\ cycle},$$

where:

$V_{RMS}$ = RMS voltage required on the input winding $= \dfrac{\text{Desired primary voltage}}{\text{Transformer turns ratio}}$;

$V_{peak}$=Peak voltage across winding=$V_{battery}-V_{drop}$;
$V_{drop}$=Voltage drop in the inverter path;
$\tau_{half\ cycle}$=½ of an operating line frequency of said ferroresonant transformer; and $\dfrac{\tau_{on}}{\tau_{half\ cycle}}$ = duty cycle.

27. The power supply of claim 23, wherein said controller operates to control said inverter in open loop with respect to said output winding.

28. The power supply of claim 23, wherein said controller is adapted to control said inverter to alternate between a power pulse and a freewheel mode of operation.

29. The power supply of claim 23, wherein said plurality of controllable switches comprises four switches configured in an H-bridge configuration.

30. The power supply of claim 23, wherein said plurality of controllable switches comprises three switches configured in a push-pull configuration.

31. The power supply of claim 23, further comprising at least two tap changers, each having an input adapted to be coupled to a source of ac power and an output, and wherein said ferroresonant transformer further comprises a utility input winding having at least two taps associated therewith, and wherein each of said outputs of said at least two tap changers are coupled to one of said at least two taps.

32. The power supply of claim 31, wherein said controller further controls selection of one of said at least two tap changers based on a monitored voltage of the source of ac power.

33. The power supply of claim 23, wherein said ferroresonant transformer further comprises a compensation winding coupled in series with said output winding.

34. The power supply of claim 31, wherein said utility input winding further comprises at least three winding taps, and further comprising at least three tap changers interposed between said at least three winding taps and the source of ac power.

35. The power supply of claim 34, wherein said controller is adapted to utilize at least three predetermined threshold values to determine a proper configuration of said tap changers.

36. The power supply of claim 34, wherein said tap changers are solid state switching devices.

37. The power supply of claim 34, wherein said tap changers are electromechanical devices, the power supply further comprising a static switch interposed between said tap changers and the source of ac power.

38. The power supply of claim 34, wherein each of said winding taps is positioned approximately 15% from an adjacent winding tap.

39. The power supply of claim 34, wherein said transformer comprises a first, a second, and a third winding tap, and wherein said first winding tap is positioned on said utility input winding to provide a first turns ratio, wherein said second winding tap is positioned on said utility input winding to provide a second turns ratio, and wherein said third winding tap is positioned on said utility input winding to provide a third turns ratio, said first turns ratio being approximately 15% less than said second turns ratio and said third turns ratio being approximately 15% greater than said second turns ratio.

40. The power supply of claim 39, wherein said first turns ratio is approximately 88% of said second turns ratio and said third turns ratio is approximately 115% of said second turns ratio.

41. The power supply of claim 31, wherein said controller is adapted to control said tap-changers to maintain a maximum voltage swing across said first input winding to approximately +/−10%.

42. A ferroresonant transformer for use in a power supply that supplies electric power to output connected loads from a utility ac input, the utility ac input having a regulated voltage range bound by an upper and a lower voltage value, the ferroresonant transformer comprising:

a ferromagnetic core;

a first primary winding wound on said core, said first primary winding having a first and a second tap coupled thereto;

an output winding wound on said core and separated from said primary winding by a first magnetic shunt; and wherein said core contains an amount of ferromagnetic material insufficient to prevent saturation of said primary winding at the upper voltage value of the utility voltage range when the upper voltage value of the utility voltage range is coupled to said second tap.

43. The transformer of claim 42, wherein said primary winding comprises a wire of a size insufficient to prevent overheating of said primary winding at the lower voltage value of the utility voltage range when the lower voltage value of the utility voltage range is coupled to said first tap at rated load.

44. The transformer of claim 42, further comprising a compensation winding wound on said core and separated from said output winding by a second magnetic shunt, said compensation winding coupled to said output winding; and an output tank capacitor coupled to said output winding and said compensation winding, said output tank capacitor having a VA rating; and wherein said VA rating of said tank capacitor is insufficient to regulate an output of the transformer over the utility voltage range without selectively switching the utility ac input between said first and said second taps.

45. The transformer of claim 42, further comprising a third tap coupled to said first primary winding, and wherein said core contains an amount of ferromagnetic material insufficient to prevent saturation of said primary winding at the upper voltage value of the utility voltage range when the upper voltage value of the utility voltage range is coupled to one of said second and said third taps.

46. The transformer of claim 42, further comprising a third tap coupled to said first primary winding, and wherein said primary winding comprises a wire of a size insufficient to prevent overheating of said primary winding at the lower voltage value of the utility voltage range when the lower voltage value of the utility voltage range is coupled to one of said first and said second taps at rated load.

47. The transformer of claim 42, further comprising:

a third tap coupled to said first primary winding;

a compensation winding wound on said core and separated from said output winding by a second magnetic shunt, said compensation winding coupled to said output winding; and an output tank capacitor coupled to said output winding and said compensation winding, said output tank capacitor having a VA rating; and wherein said VA rating of said tank capacitor is insufficient to regulate an output of the transformer over the utility voltage range without selectively switching the utility ac input between said first, said second, and said third taps.

48. The transformer of claim 45, wherein said first tap is positioned approximately 15% from said second tap, and said second tap is positioned approximately 15% from said third tap.

49. The transformer of claim 45, wherein said first tap is positioned on said first primary winding to provide a first turns ratio, wherein said second tap is positioned on said first primary winding to provide a second turns ratio, and wherein said third tap is positioned on said utility input winding to provide a third turns ratio, said first turns ratio being approximately 15% less than said second turns ratio and said third turns ratio being approximately 15% greater than said second turns ratio.

50. The transformer of claim 49, wherein said first turns ratio is approximately 88% of said second turns ratio and said third turns ratio is approximately 115% of said second turns ratio.

51. The transformer of claim 45, wherein said taps are positioned on said first input winding to maintain a maximum voltage swing across said first input winding to approximately +/−10% over the regulated voltage range.

52. The transformer of claim 45, further comprising a second input winding wound on said core.

53. The transformer of claim 45, further comprising a compensation winding wound on said core and separated from said output winding by a magnetic shunt.

54. The transformer of claim 53, wherein said compensation winding is coupled in series with said output winding.

55. The transformer of claim 45, wherein said ferromagnetic core comprises a first number of steel laminations, and wherein said first number is substantially less than a second number of steel laminations required to prevent saturation of said primary winding over the regulated voltage range of the utility ac input without said taps.

56. The transformer of claim 55, wherein said first number of steel laminations is approximately 20% less than said second number of steel laminations.

57. The transformer of claim 56, wherein said first number of steel laminations is approximately 30% less than said second number of steel laminations.

* * * * *